(12) United States Patent
Gloeckner et al.

(10) Patent No.: US 10,646,641 B1
(45) Date of Patent: May 12, 2020

(54) LIQUID DISPENSING PUMP

(71) Applicant: Micromo Electronics, Inc., Clearwater, FL (US)

(72) Inventors: Robert Gloeckner, Clearwater, FL (US); Isaac Diggs, Clearwater, FL (US)

(73) Assignee: Micromo Electronics, Inc., Clearwater, FL (US)

( * ) Notice: Subject to any disclaimer, the term of this patent is extended or adjusted under 35 U.S.C. 154(b) by 271 days.

(21) Appl. No.: 15/660,350

(22) Filed: Jul. 26, 2017

(51) Int. Cl.
*A61M 5/145* (2006.01)
*A61M 5/142* (2006.01)
*A61M 5/315* (2006.01)
*F04B 43/12* (2006.01)
*F04B 43/067* (2006.01)

(52) U.S. Cl.
CPC .... *A61M 5/14236* (2013.01); *A61M 5/14566* (2013.01); *A61M 5/315* (2013.01); *A61M 5/31535* (2013.01); *F04B 43/067* (2013.01); *F04B 43/1269* (2013.01)

(58) Field of Classification Search
CPC ................. A61M 5/145; A61M 5/1452; A61M 2205/3317; A61M 2205/332
See application file for complete search history.

(56) References Cited

U.S. PATENT DOCUMENTS

| | | | |
|---|---|---|---|
| 7,246,850 | B2 | 7/2007 | Steele |
| 7,360,999 | B2 | 4/2008 | Nelson et al. |
| 7,375,509 | B2 | 5/2008 | Meaney |
| 7,452,190 | B2 | 11/2008 | Bouton et al. |
| 7,975,562 | B2 | 7/2011 | Skarpil |
| 8,282,595 | B2 | 10/2012 | Wagner |
| 8,366,371 | B2 | 2/2013 | Maniscalco et al. |
| 8,366,670 | B2 | 2/2013 | Neer |
| 8,663,164 | B2 | 3/2014 | Neer et al. |
| 9,194,388 | B2 | 11/2015 | Laermer et al. |
| 9,517,303 | B2 | 12/2016 | Bazargan et al. |
| 2002/0077598 | A1* | 6/2002 | Yap ..................... A61M 5/1456 604/155 |
| 2012/0078181 | A1* | 3/2012 | Smith ................ A61M 5/14216 604/152 |
| 2014/0257178 | A1 | 9/2014 | Lee et al. |
| 2016/0339171 | A1 | 11/2016 | Trock et al. |
| 2017/0028124 | A1 | 2/2017 | Deak et al. |
| 2017/0056581 | A1 | 3/2017 | Deak et al. |

* cited by examiner

*Primary Examiner* — Laura A Bouchelle
(74) *Attorney, Agent, or Firm* — Allen Dyer Doppelt & Gilchrist, PA

(57) ABSTRACT

A liquid dispensing pump includes a lead screw having a lead screw shaft extending along a lead screw axis, and the lead screwing is operably connected to a piston connected to a liquid reservoir. A thrust bearing is connected to the lead screw and configured to support an axial force on the lead screw when dispensing liquid. A magnet is engaged to the thrust bearing so as to move in response to the axial force on the lead screw. A magnetic transducer is mounted in proximity to the magnet and configured to generate an output signal in responsive to the magnet move.

19 Claims, 7 Drawing Sheets

LIQUID DISPENSING PUMP

FIELD OF THE INVENTION

The present invention relates to liquid dispensing pumps, and more particularly, to liquid pumps that use a magnetic transducer to measure liquid dosage.

BACKGROUND OF THE INVENTION

Liquid dispensing pumps, especially micro-dosing liquid pumps, are often complicated in structure and expensive to make. They are often used in medical field to deliver a controlled amount of a liquid medication or fluid to a patient. Liquid dispensing pumps in medicine must meet very high precision dispensing criteria to ensure patient safety. A common example of this type of pump is an automatic insulin injection pump. Usually, the pressure or force on a leadscrew of the pump is measured by a compressible resistor, which is both expensive and requires electrical connections to penetrate the pump housing. This will make the pump less robust. While currently available liquid pumps are useful, further improvements are possible.

SUMMARY OF THE INVENTION

In view of the foregoing, it is an object of the present invention to provide improved micro-dosing pumps. According to one embodiment of the present invention, a liquid dispensing pump includes a leadscrew having a leadscrew shaft extending along a leadscrew axis, and the leadscrew is operably connected to a piston connected to a liquid reservoir. A thrust bearing is connected to the leadscrew and configured to support an axial force on the leadscrew when dispensing liquid. A magnet is engaged to the thrust bearing so as to move in response to the axial force on the leadscrew. A magnetic transducer is mounted in proximity to the magnet and configured to generate an output signal in response to the magnet move.

According to another embodiment of the present invention, a method for determining amount of dispensing liquid using a liquid dispensing pump includes applying an axial force on a leadscrew of the liquid dispensing pump when dispensing liquid, and displacing a magnet connected to the leadscrew in response to the axial force on the leadscrew. An output signal is generated via a magnetic transducer mounted in proximity to the magnet based on the displacement of the magnet. The output signal of the magnetic transducer then determines the amount of liquid dispensed.

These and other objects, aspects and advantages of the present invention will be better appreciated in view of the drawings and following detailed description of preferred embodiments.

DETAILED DESCRIPTION OF PREFERRED EMBODIMENTS

Figure 1:
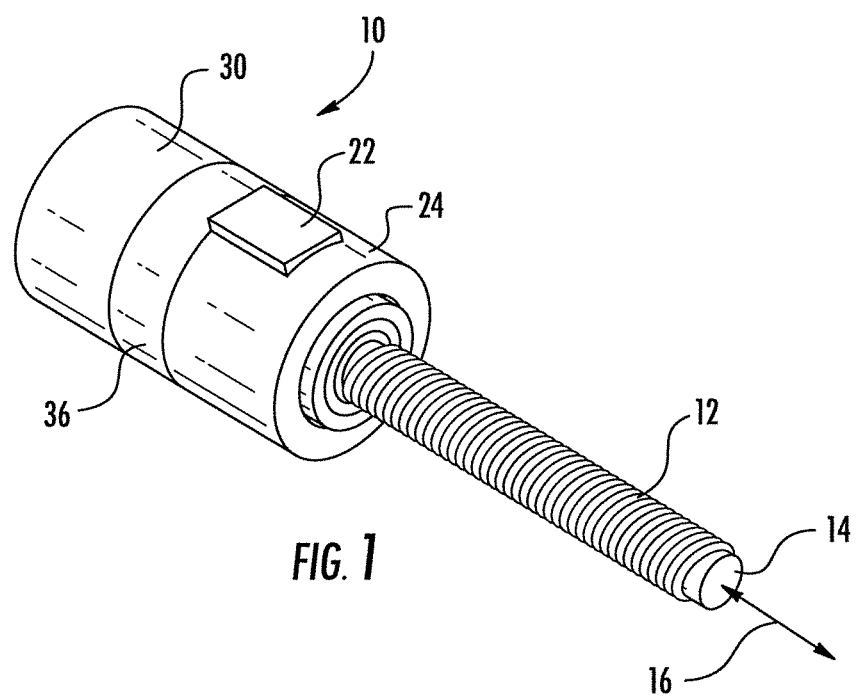
FIG. 1 is a perspective view of a liquid dispensing pump according to one embodiment of the present invention.
Figure 2:
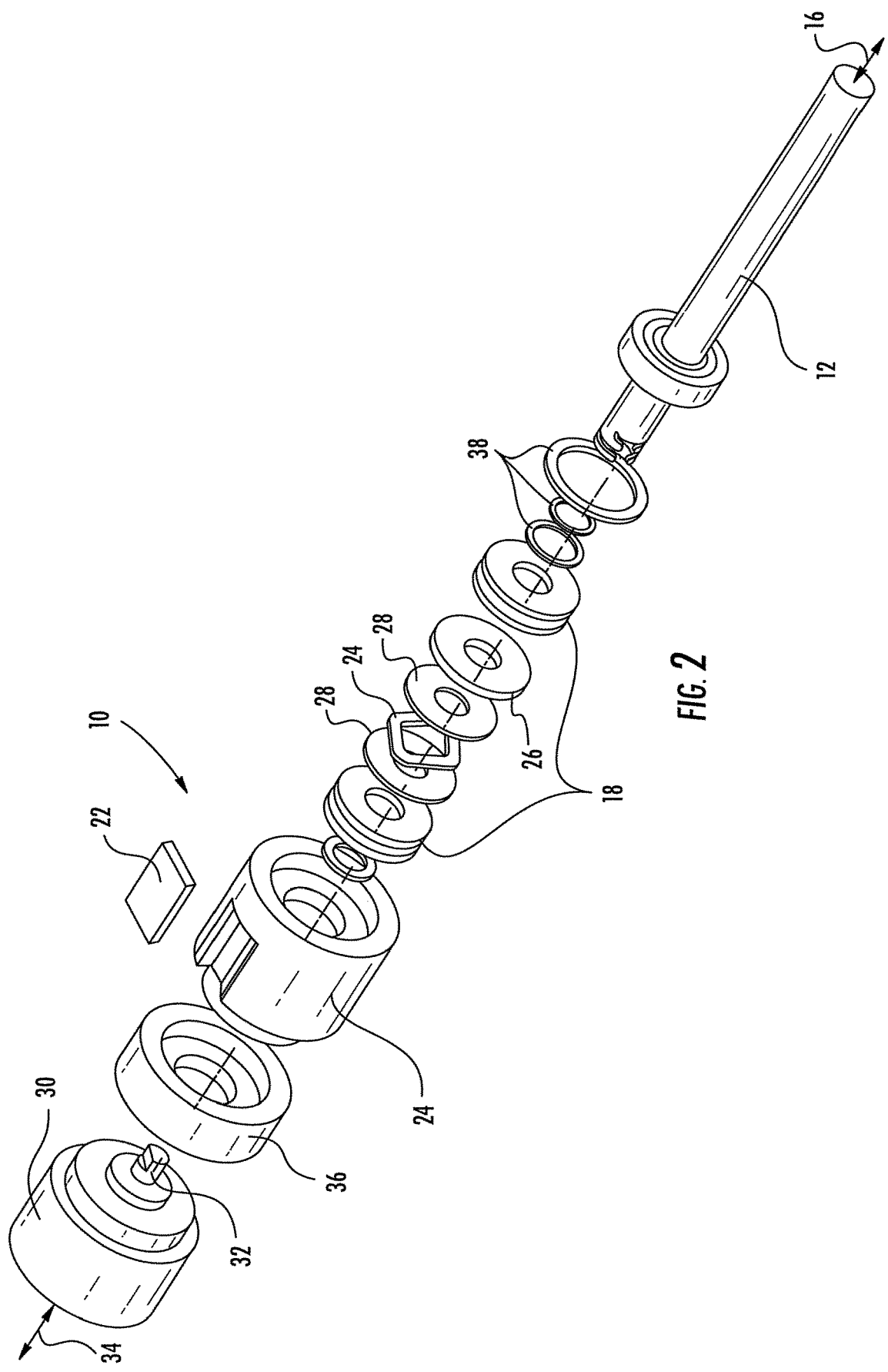
FIG. 2 is an exploded view of the liquid dispensing pump of FIG. 1.
Figure 3:
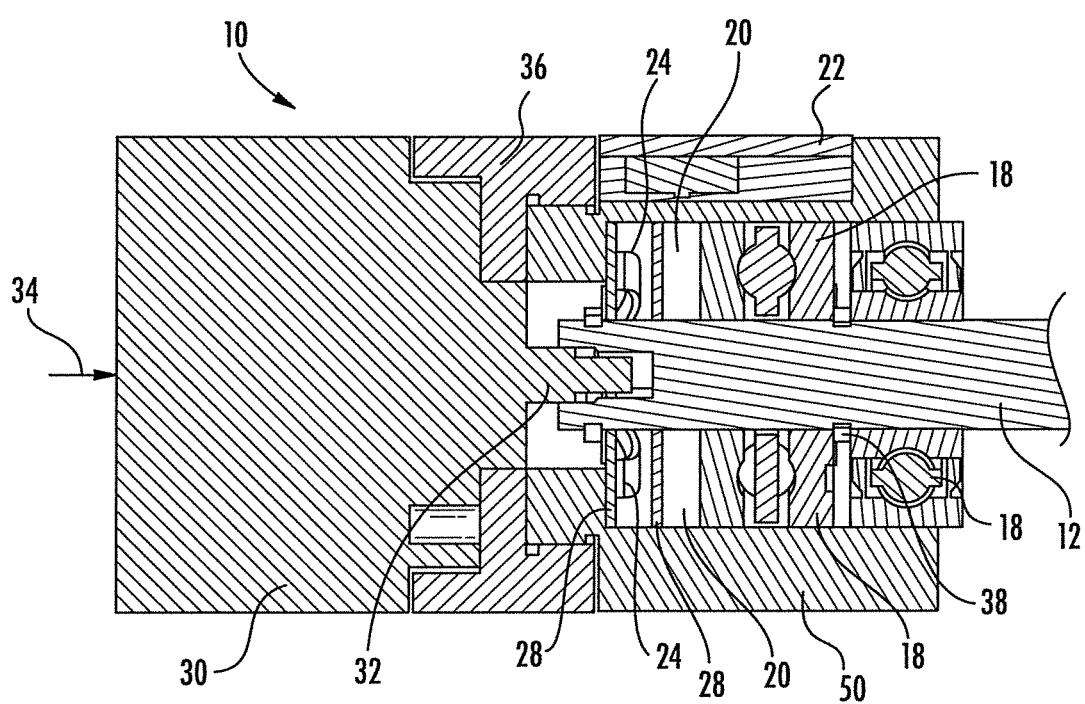
FIG. 3 is a cross sectional view of the liquid dispensing pump of FIG. 1.

Referring to FIGS. 1-3, according to one embodiment of the invention, a liquid dispensing pump 10 includes a leadscrew 12 having a leadscrew shaft 14 extending along a leadscrew axis 16. The leadscrew 12 is operably connected to a plunger or piston connected to a liquid reservoir (not shown). A thrust bearing 18 is connected to the leadscrew 12 and configured to support an axial force applied thereon. A magnet 20 is engaged to the thrust bearing 18 so as to move in response to the axial force on the leadscrew 12. A magnetic transducer 22 is mounted in proximate to the magnet 20 and configured to generate an output signal in responsive to the movement of the magnet 20.

In the depicted embodiment, the thrust bearing 18 includes two double-direction thrust ball bearings on both sides of the magnet 20. However, other types and arrangements of the magnet 20 and thrust bearings 18 can also be used.

The magnet 20 includes an elastic member 24 (e.g., a wave spring) and a magnetic member 26 coaxially mounted around the leadscrew shaft 14. At least one washer 28 is mounted coaxially between the elastic member 24 and the magnetic member 26 to provide an even pressure distribution there between.

The magnetic transducer 22 is preferably a Hall-effect sensor that monitors the position of magnet 20 relative to itself. The magnet transducer 22 can sense the magnetic field generated by the magnet 20. The motion/position of magnet 20 is used to detect the position of the leadscrew 12 and therefore the plunger or piston connected to the leadscrew 12. The magnetic transducer 22 is configured to be in signal communication with a processor (not shown). The processor is configured to receive an output signal from the magnetic transducer 22 and determine operating conditions of pump 10, specifically, the amount of liquid dispensed by the pump 10.

When liquid is dispensed, an axial force is applied on the leadscrew 12, generating a displacement of the magnet 20 along the leadscrew shaft 12. Specifically, the displacement of the magnetic member 26 causes a deflection of the elastic member 24 (e.g., wave spring). The displacement of the magnet 20 is determined by the magnetic transducer 22 and indicated by an output signal (e.g., a voltage signal). The deflection of the elastic member 24 is proportional to the load applied thereon, and the load on the elastic member 24 is proportional to the amount of liquid dispensed. The amount of dispensed liquid is thus correlated with the output signal of the magnetic transducer 22.

The liquid dispensing pump 10 can further include a motor 30 having an output shaft 32 extending along an output shaft axis 34. The motor output shaft 32 is operable to rotate the leadscrew shaft 14. In the depicted embodiment, the motor output shaft 32 is coaxial with the leadscrew shaft 14. In the depicted embodiment, the motor 30 is connected to the pump housing 50 via a ring 36.

The thrust bearing 18, the magnet 20, and a portion of the leadscrew 12 and other suitable components such as rings, shims or gaskets 38 are arranged inside the pump housing 50, and the magnetic transducer 22 is mounted on the outer surface of the pump housing 50 in proximity to the magnet 20.

The pump 10 can further include a control unit (not shown) connected between the motor 30 and the magnetic transducer 22 so that the control unit receives signals from the magnet transducer 22 and controls direction and velocity of the motor output shaft 32. The control unit can be used to delivery of specific amount of liquid dispensed in high precision.

In connection with the following description of alternative embodiments, the same reference numbers are applied to corresponding elements in the above-described embodiment, followed by a suffix specific to the alternative embodiment (e.g., magnetic transducer 22, magnetic transducer 22A, magnetic transducer 22B).

Figure 4:
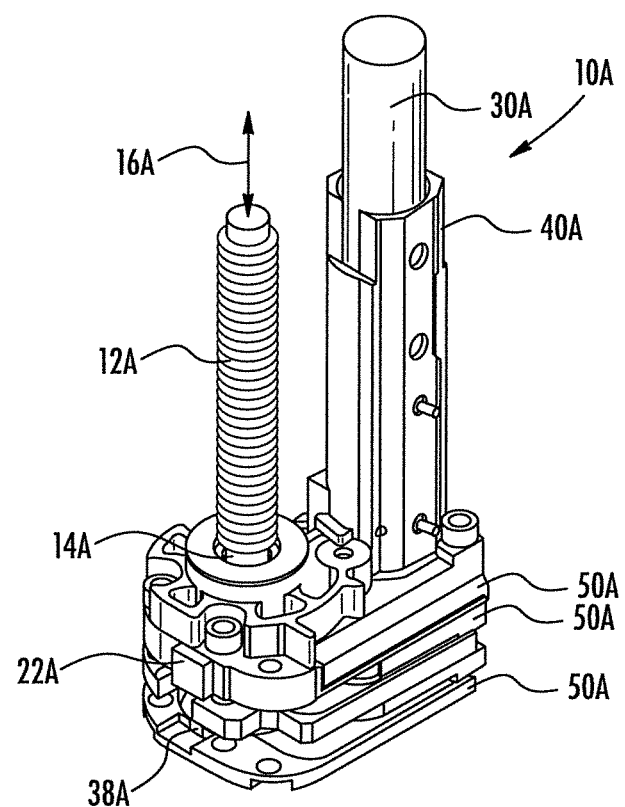
FIG. 4 is a perspective view of a liquid dispensing pump according to another embodiment of the present invention.
Figure 5:
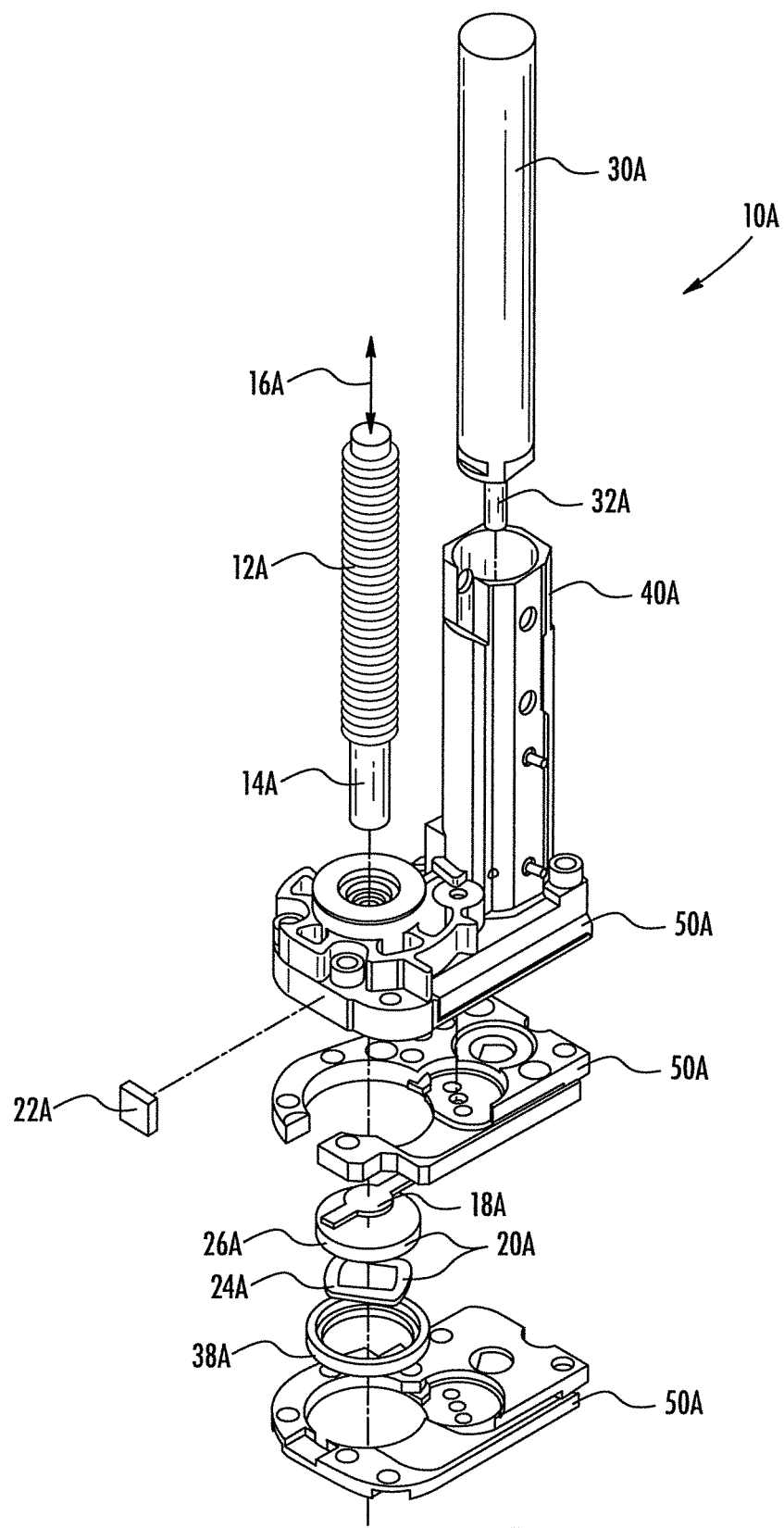
FIG. 5 is an exploded view of the liquid dispensing pump of FIG. 4.
Figure 6:
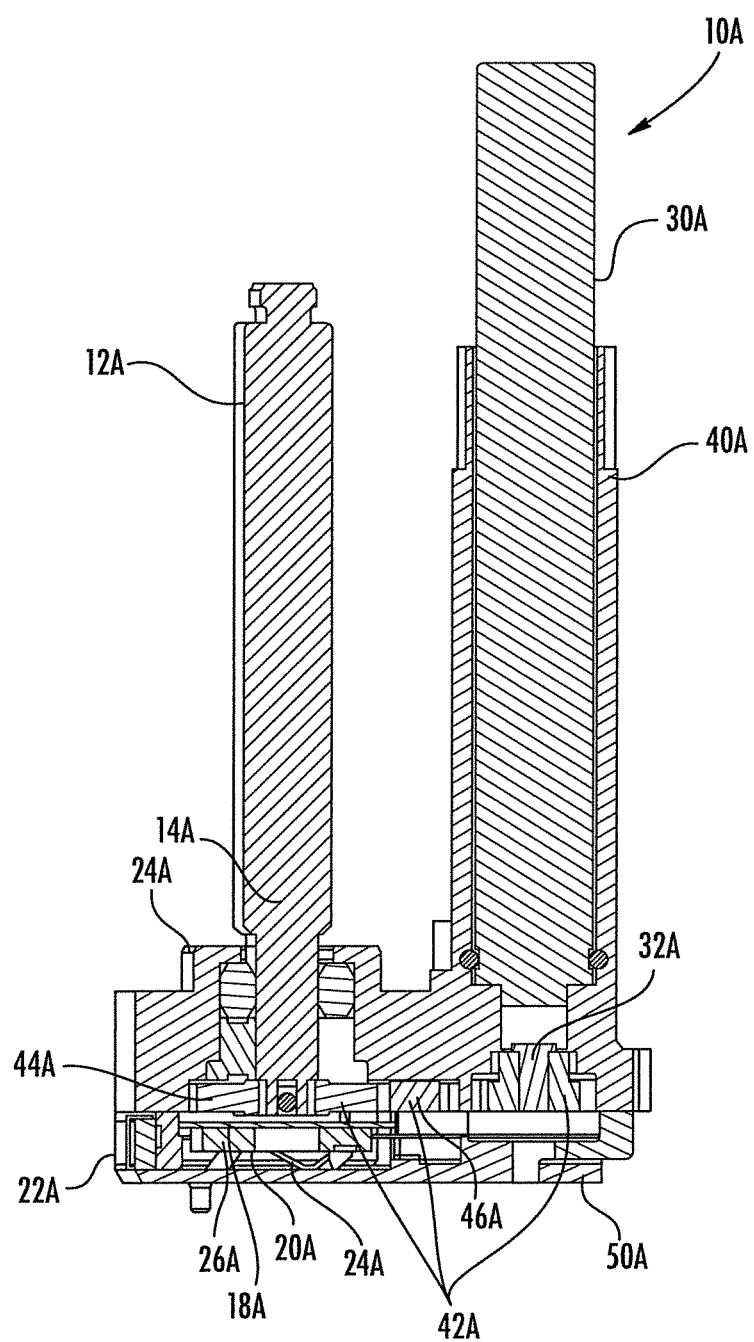
FIG. 6 is a cross sectional view of the liquid dispensing pump of FIG. 4.

FIGS. 4-6 illustrate an alternative embodiment of the liquid dispensing pump 10A. The magnet 20A includes the elastic member 24A and the magnetic member 26A. The magnet 20A and the thrust bearing 18A function the same way as those depicted in FIGS. 1-3, except the liquid dispensing pump 10A is driven by a motor output shaft 32A that is offset therefrom the leadscrew shaft 14A. In the depicted embodiment, the motor output shaft 32A is situated in a motor housing 40A and parallel with the leadscrew shaft 14A.

The motor output shaft 32A can be configured to rotate the leadscrew shaft 14A via a gear arrangement 42A. For example, the gear arrangement 42A includes a first gear 44A mounted around the motor output shaft 32A and operable to drive a second gear 46A mounted around the leadscrew shaft 14A. Other gear arrangement can be used. In the depicted embodiment, the first gear 44A mounted around the motor output shaft 32A is operable to drive the second gear 46A mounted around the leadscrew shaft 14A via a third gear 48A coupled between the first gear 44A and the second gear 46A. The third gear 48A can include one or more gears which reduce (or increase) the rotational speed generate by the first gear 44A to a rotational speed input to a second gear 46A that drives the leadscrew 12A. The thrust bearing 18A, the elastic member 24A, the magnetic member 26A, the gear arrangement 42A, and other suitable components can be situated in a pump housing 50A.

Figure 7:
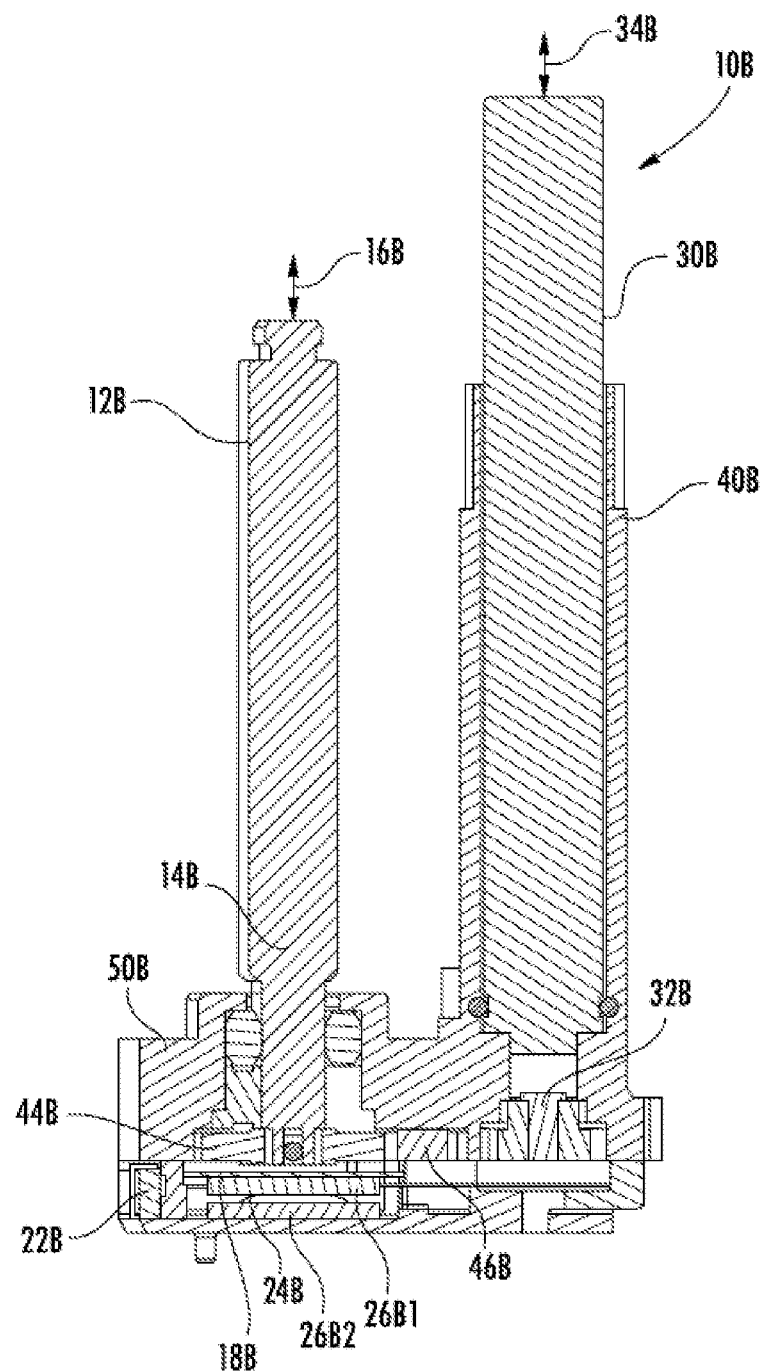
FIG. 7 is a cross sectional view of a liquid dispensing pump according to another embodiment of the present invention.

According to another embodiment of the present invention, referring to FIG. 7, the liquid dispensing pump 10B is the same as the system 10A as depicted in FIGS. 4-6, except the magnet 20B includes two opposing magnetic members 26B1 and 26B2 with an elastic member 24B (e.g., wave spring) inserted therebetween. In this scenario, the axial force on the leadscrew 12B will change the relative position between the opposing magnets 26B1 and 26B2, and the distance change between the opposing magnetic members 26B1 and 26B2 can be determined by the magnetic transducer 22B. The distance change between the opposing magnetic members 26B1 and 26B2 will translate the deflection of the elastic member 24B therebetween and therefore correlate to the amount of liquid dispensed.

The pump can enable the measurement of the amount of liquid dispensed without requiring contact between a magnetic transducer and a magnet inside a pump housing. As such, the pump housing can be sealed without cables, wires or other connector between inside and outside of the pump housing. The contactless design of the liquid dispensing avoids movement of the magnetic transducer when force or load is applied. The structure design of the pump makes it less expensive to manufacture and more robust in use. The liquid dispensing pump of the present invention has an accurate and reliable performance with less drift and hysteresis.

The foregoing is provided for illustrative and exemplary purposes; the present invention is not necessarily limited thereto. Rather, those skilled in the art will appreciate that various modifications, as well as adaptations to particular circumstances, are possible within the scope of the invention as herein shown and described.

What is claimed is:

1. A liquid dispensing pump comprising:
   a lead screw having a lead screw shaft extending along a lead screw axis, the lead screw being operably connected to a piston connected to a liquid reservoir;
   a thrust bearing connected to the lead screw and configured to support an axial force on the lead screw when dispensing liquid;
   a magnet engaged to the thrust bearing so as to move in response to the axial force on the lead screw; and
   a magnetic transducer mounted in proximity to the magnet and configured to generate an output signal responsive to movement of the magnet;
   wherein the magnetic transducer is mounted on an outer surface of a pump housing.

2. The liquid dispensing pump of claim 1, further comprising a motor having an output shaft extending along an output shaft axis, wherein the motor output shaft is operable to rotate the lead screw shaft.

3. The liquid dispensing pump of claim 2, wherein the motor output shaft is coaxial with the lead screw shaft.

4. The liquid dispensing pump of claim 2, wherein the motor output shaft is offset to the lead screw shaft.

5. The liquid dispensing pump of claim 4, wherein the motor output shaft is parallel to the lead screw shaft.

6. The liquid dispensing pump of claim 4, wherein the motor output shaft is configured to rotate the lead screw shaft via a gear arrangement.

7. The liquid dispensing pump of claim 6, wherein the gear arrangement includes a first gear mounted around the motor output shaft configured to drive a second gear mounted around the lead screw shaft.

8. The liquid dispensing pump of claim 6, wherein the gear arrangement includes a first gear mounted around the motor output shaft configured to drive a second gear mounted around the lead screw shaft via a third gear coupled between the first gear and the second gear.

9. The liquid dispensing pump of claim 1, wherein the liquid dispensing pump further include a processor configured to convert the output signal of the magnet transducer to an amount of dispensed liquid.

10. The liquid dispensing pump of claim 1, wherein the magnet includes an elastic member and a magnetic member coaxially mounted around the lead screw shaft.

11. The liquid dispensing pump of claim 10, wherein the elastic member is a wave spring.

12. The liquid dispensing pump of claim 1, wherein the magnet includes two opposing magnet members with an elastic member positioned therebetween.

13. The liquid dispensing pump of claim 1, wherein the magnetic transducer includes a Hall-effect sensor.

14. A method for determining amount of dispensing liquid using a liquid dispensing pump, the method comprising:
    applying an axial force on a lead screw of the liquid dispensing pump when dispensing liquid;
    displacing a magnet connected to the lead screw in response to the axial force on the lead screw;

generating an output signal via a magnetic transducer mounted in proximity to the magnet based on the displacement of the magnet; and determining amount of dispensed liquid based on the output signal of the magnetic transducer;

wherein displacement of the magnet includes a displacement of two opposing magnetic members engaged with an elastic member therebetween.

15. The method of claim 14, wherein displacement of the magnet includes a displacement of a magnetic member engaged with an elastic member.

16. The method of claim 14, wherein determining amount of dispensed liquid based on the output of the magnetic transducer includes determining a load on the elastic member.

17. The method of claim 14, wherein the magnetic transducer includes a Hall-effect sensor.

18. The method of claim 14, wherein the magnetic transducer is located on an outer surface of a pump housing.

19. A liquid dispensing pump comprising:

a lead screw having a lead screw shaft extending along a lead screw axis, the lead screw being operably connected to a piston connected to a liquid reservoir;

a thrust bearing connected to the lead screw and configured to support an axial force on the lead screw when dispensing liquid;

a magnet engaged to the thrust bearing so as to move in response to the axial force on the lead screw; and a magnetic transducer mounted in proximity to the magnet and configured to generate an output signal responsive to movement of the magnet;

wherein the magnet includes an elastic member and a magnetic member coaxially mounted around the lead screw shaft; and wherein the elastic member is a wave spring.

\* \* \* \* \*